United States Patent [19]
Mais et al.

[11] Patent Number: 4,851,596
[45] Date of Patent: Jul. 25, 1989

[54] PROCESS FOR NUCLEUS-CHLORINATION OF AROMATIC HYDROCARBONS

[75] Inventors: Franz-Josef Mais, Duesseldorf; Helmut Fiege, Leverkusen; Kai Röhlk, Bergisch Gladbach; Karlfried Wedemeyer, Cologne, all of Fed. Rep. of Germany

[73] Assignee: Bayer Aktiengesellschaft, Leverkusen, Fed. Rep. of Germany

[21] Appl. No.: 192,739

[22] Filed: May 11, 1988

[30] Foreign Application Priority Data

May 28, 1987 [DE] Fed. Rep. of Germany ....... 3718060

[51] Int. Cl.$^4$ ............................................. C07C 17/12
[52] U.S. Cl. .................................. 570/209; 570/206; 570/207; 570/208; 570/210
[58] Field of Search ............... 570/207, 208, 209, 210, 570/206

[56] References Cited

U.S. PATENT DOCUMENTS

| 3,226,447 | 12/1965 | Bing et al. | 570/209 |
| 4,031,144 | 6/1977 | Bella | 570/209 |
| 4,031,147 | 6/1977 | Graham | 570/209 |
| 4,069,263 | 1/1978 | Lin | 570/209 |
| 4,250,122 | 2/1981 | Lin et al. | 570/209 |
| 4,289,916 | 9/1981 | Nakayama et al. | 570/209 |

FOREIGN PATENT DOCUMENTS 0126669 11/1984 European Pat. Off. .

*Primary Examiner*—Werren B. Lone
*Attorney, Agent, or Firm*—Sprung Horn Kramer & Woods

[57] ABSTRACT

Aromatic hydrocarbons are chlorinated in the nucleus in the presence of Friedel-Crafts catalysts and in the presence of co-catalysts in the liquid phase by using thiazepines as co-catalysts.

18 Claims, No Drawings

PROCESS FOR NUCLEUS-CHLORINATION OF AROMATIC HYDROCARBONS

BACKGROUND OF THE INVENTION

The invention relates to a process for nucleus-chlorination of aromatic hydrocarbons in the presence of Friedel-Crafts catalysts and in the presence of co-catalysts in the liquid phase.

The reaction of aromatic hydrocarbons, such as toluene, in the liquid phase with gaseous chlorine to give nucleus-substituted chlorine derivatives, such as monochlorotoluene, is known from the literature (Ullmanns Encyklopädie der technischen Chemie (Ullmann's Encyclopedia of Industrial Chemistry), 4th edition, Volume 9, page 499 et seq.). The chlorination is in general carried out in the presence of Friedel-Crafts catalysts, such as iron(III) chloride, antimony chlorides or aluminium chloride. The resulting chlorination product is usually a mixture of monochlorinated and polychlorinated position isomer compounds. Thus, for example, a mixture of monochlorotoluenes and dichlorotoluenes is obtained in the chlorination of toluene catalyzed with iron(III) chloride. The main product in the monochlorotoluene fraction is o-chlorotoluene. This fraction also contains p-chlorotoluene and a small amount of m-chlorotoluene.

Since p-chloroalkylbenzenes in particular, such as p-chlorotoluene, are useful intermediate products, there has in the past been no lack of attempts to steer the chlorination such that the ratio of o- to p-chloroalkylbenzenes is reduced, that is to say attempts have been made to discover conditions which promote the formation of p-chloroalkylbenzenes.

It is known from U.S. Pat. No. 3,226,447 that an o/p ratio of 1.2 can be obtained by adding sulphur compounds with divalent sulphur to the Friedel-Crafts catalyst in the chlorination of, for example, toluene. A disadvantage of this process is the fact that this favourable ratio is achieved only when antimony salts are used as the Friedel-Crafts catalysts. It is furthermore a disadvantage that, according to Example 16, the amounts of catalyst components used are very high, that is to say 1% by weight for each of the two components. Another disadvantage is that the o/p ratio is still significantly greater than 1, that is to say more o-compound than p-compound is formed.

The chlorination of toluene with Friedel-Crafts catalysts or compounds which form Friedel-Crafts catalysts under the reaction conditions with the addition of sulphur or sulphur compounds, such as sulphur halides, is described in DE-OS (German Published Specification) No. 1,543,020 and U.S. Pat. No. 4,031,144. A ratio of o/p for the chlorination of toluene of 1.03–1.10 is thereby obtained (see the example table of U.S. Pat. No. 4,031,144). The amounts used are, for example according to Example 9 of DE-OS (German Published Specification) No. 1,543,020, 0.05% by weight of $S_2Cl_2$ and 0.10% by weight of $FeCl_3$. A disadvantage of this process is that the o/p ratio is still unsatisfactorily high.

The chlorination of toluene with Friedel-Crafts catalysts with the addition of thianthrenes or substituted thianthrenes is known from U.S. Pat. No. 4,031,147, U.S. Pat. No. 4,069,263, U.S. Pat. No. 4,069,264 and U.S. Pat. No. 4,250,122. The favourable o/p ratios which can be achieved for the chlorination of, for example, toluene are about 0.7. The disadvantage of this process, however, is that this favourable ratio is achieved either only by using antimony salts as the Friedel-Crafts catalyst or, in the case of the use of iron salts as the catalysts, only at very low reaction temperatures of about 0° C. (see Example 14 of U.S. Pat. No. 4,250,122 and Examples 2–4 of U.S. Pat. No. 4,069,263). Both circumstances are industrially decidedly unfavourable. When antimony salts are used, the co-catalytic effect of the thianthrenes is greatly hindered by the traces of iron which are to be avoided industrially only at exceptional expense (in this context, see U.S. Pat. No. 4,024,198). In addition, the reaction is so highly exothermic that removal of the heat at about 0° C. is very expensive (cooling with brine). A further disadvantage is that—as taught in DE-OS (German Published Specification ) No. 3,023,437—the thianthrenes are already destroyed by the ubiquitous traces of water under the customary reaction conditions and thus lose their activity.

The chlorination of toluene in the presence of Lewis acids and phenoxathiines as the catalyst system is known from the Patent Specifications U.S. Pat. No. 4,289,916, European Pat. No. 0,063,394 and European Pat. No. 0,173,222. The o/p ratio which can be achieved is in one case 0.6 (see Example 1 of European Pat. No. 0,173,222). A disadvantage here is, however, the industrially extremely unfavourable use of antimony chloride and the high amount of 0.29% by weight of co-catalyst used (see Example 1 of European Pat. No. 0,173,222). If iron(III) chloride is used instead of antimony chloride, an o/p ratio of 0.68 results (see Example 3 of European Pat. No. 0,173,222), but this in turn is obtained only at the industrially extremely unfavourable low reaction temperature of 5° C. At the industrially advantageous reaction temperature of 50° C., the o/p ratio with the phenoxathiine derivative claimed in European Pat. No. 0,173,222 in the presence of iron(III) chloride is only 0.88, as experiments carried out by ourselves show (see Example 40). In the other two patent publications (U.S. Pat. No. 4,289,916 and European Pat. No. 0,063,384), the best examples are described with amounts of in each case 0.05% by weight of iron(III) chloride and 0.05% by weight of a phenoxathiine derivative used at a reaction temperature of 35° C. and a most favourable o/p ratio of about 0.8. If the industrially less favourable antimony chlorides are used here instead of iron(III) chloride, the o/p ratio can be reduced down to 0.65 at a reaction temperature of 20° C. (see Example No. 16 of European Pat. No. 0,063,384). The disadvantage is, however, that phenoxathiines are also destroyed in the presence of traces of water.

The chlorination of toluene in the presence of Friedel-Crafts catalysts and N-substituted phenothiazines is known from the patent specification European Pat. No. 0,126,669. According to the most favourable example (see Example No. 1 of European Pat. No. 0,126,669), an o/p ratio of 0.84 results at a reaction temperature of 30° C. using amounts of 0.011% by weight of iron(III) chloride and 0.028% by weight of co-catalyst. The o/p isomer ratio in this process is still unfavourably high.

The chlorination of, for example, toluene in the presence of certain zeolites is known from European Pat. No. 0,112,722 and European Pat. No. 0,154,236. The o/p ratio is about 0.3 when, for example, halogenocarboxylic acid halides are added as moderators. The considerable amounts of 5% by weight of zeolite and 1% by weight of halogenocarboxylic acid halides used are a disadvantage of this process. A further considerable disadvantage is that very large amounts (up to 8% by weight) of benzyl chlorides are obtained in the mixtures obtainable, as our own experiments have shown. The formation of benzyl chlorides interferes with the subsequent customary distillative working up to a quite exceptional degree.

SUMMARY OF THE INVENTION

A process has now been found for nucleus-chlorination of aromatic hydrocarbons of the formula (I),

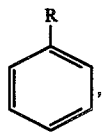
(I)

wherein R denotes an alkyl or cycloalkyl radical with up to 12 C atoms, in the presence of Friedel-Crafts catalysts and in the presence of co-catalysts in the liquid phase, which is characterized in that thiazepines are used as co-catalysts.

DETAILED DESCRIPTION OF THE INVENTION

Thiazepines which can be used in the process according to the invention are those of the formulae shown below:

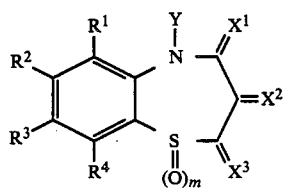
(II)

or

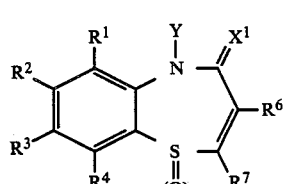
(III)

or

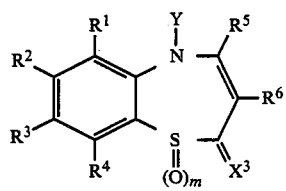
(IV)

or

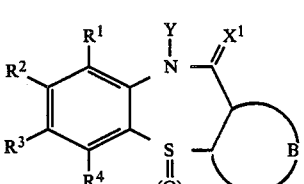
(V)

or

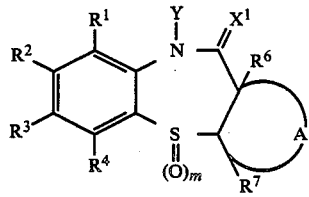
(VI)

or

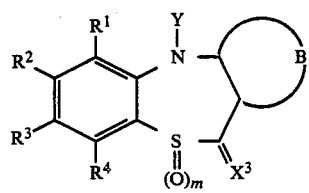
(VII)

or

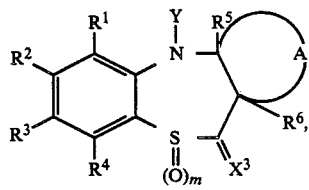
(VIII)

wherein $R^1$, $R^2$, $R^3$ and $R^4$ are identical or different and represent hydrogen, hydroxyl, amino, cyano, halogen, nitro, nitroso, sulphonyl, sulphoxyl, tosyl, mercapto, carboxyl, carboxyamide, carbalkoxy, dithiocarboxyl, thiocarboxylamide, dithiocarbalkoxy or optionally substituted alkyl, aryl, heteroaryl, alkoxy, aryloxy, heteroaryloxy, acyloxy, alkylthio, arylthio, heteroarylthio, acylthio, acyl, thioacyl or acylamino, or amongst themselves form one or more saturated or unsaturated optionally substituted isocyclic or heterocyclic carbon rings with up to 8 C atoms, Y denotes hydrogen or optionally substituted alkyl, aryl, heteroaryl, acyl, thioacyl, acyloxy, arylamino or acylamino, $X^1$, $X^2$ or $X^3$ denote the following groupings:

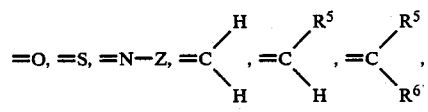

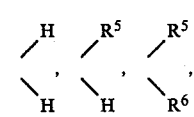

wherein $R^5$, $R^6$ and $R^7$ are identical or different and have the meaning of $R^1$ to $R^4$, with the exception that they do not form a cyclic ring amongst themselves and Z has the meaning of Y, with the exception that Z is not H, A denotes the fusing-on of an optionally substituted saturated isocyclic or heterocyclic ring with up to 8 C atoms, B denotes the fusing-on of an optionally substituted unsaturated isocyclic or heterocyclic ring with up to 8 C atoms and m denotes 0 or 1.

Thiazepines which are preferably used are those of the formula:

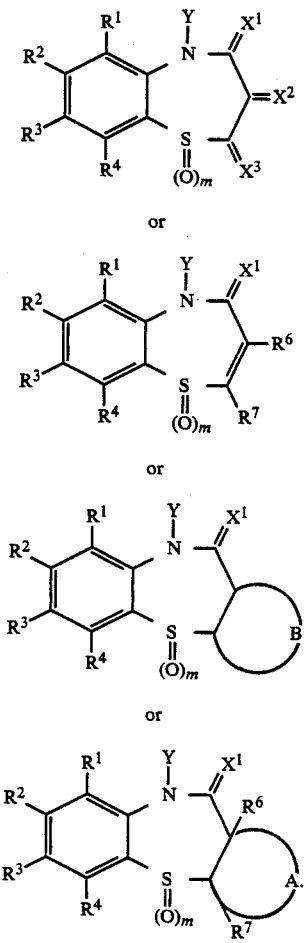

Particularly preferred thiazepines are those of the formulae:

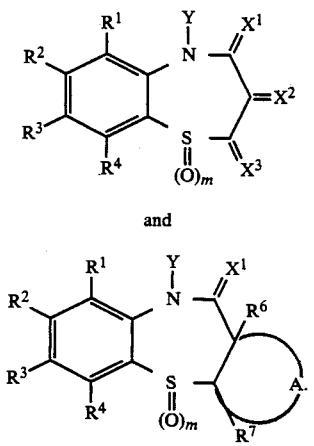

Substituents which may be mentioned for the above-mentioned radicals are: halogen, nitro, alkoxy, alkyl, aryl and heteroaryl, preferably halogen and alkyl.

Alkyl radicals which may be mentioned are those with 1 to 16 C atoms, preferably 1 to 4 C atoms, for example methyl, ethyl, n-propyl, isopropyl, n-butyl, isobutyl, t-butyl, n-pentyl, cyclopentyl, n-hexyl, cyclohexyl, n-decyl, n-tridedecyl, n-hexadecyl, benzyl, chloromethyl, dichloromethyl, trichloromethyl and trifluoromethyl, preferably methyl, n-propyl, n-tridecyl, benzyl and trifluoromethyl; aryl radicals which may be mentioned are those with 1 to 10 C atoms, preferably 1 to 7 C atoms, for example phenyl, naphthyl, tolyl, anisyl, chlorophenyl and nitrophenyl, preferably phenyl and chlorophenyl; heteroaryl radicals which may be mentioned are those with 1 to 9 C atoms, preferably 1 to 5 C atoms, for example pyridyl, methylpyridyl, furyl, pyrrolyl, imidazolyl, thienyl and indolyl, preferably furyl and imidazolyl; alkoxy radicals which may be mentioned are those with 1 to 6 C atoms, preferably 1 to 4 C atoms, for example methoxy, ethoxy, t-butoxy, cyclohexyloxy and trifluoromethoxy, preferably methoxy and ethoxy; aryloxy radicals which may be mentioned are those with 1 to 10 C atoms, preferably 1 to 7 C atoms, for example phenoxy, naphthoxy, methylphenoxy and chlorophenoxy; preferably phenoxy and chlorophenoxy; heteroaryloxy radicals which may be mentioned are those with 1 to 9 C atoms, preferably 1 to 5 C atoms, for example pyridyloxy, furyloxy and thienyloxy, preferably furyloxy; acyloxy radicals which may be mentioned are those with 1 to 7 C atoms, preferably 1 to 4 C atoms, for example acetoxy, formyloxy, benzoyloxy, trichloroacetyloxy, chlorophenylcarbonyloxy and trifluoroacetoxy, preferably acetoxy and trichloroacetoxy; alkylthio radicals which may be mentioned are those with 1 to 6 C atoms, preferably 1 to 4 C atoms, for example methylthio, ethylthio, cyclohexylthio, trifluoromethylthio and trichloromethylthio, preferably methylthio; arylthio radicals which may be mentioned are those with 1 to 7 C atoms, preferably 1 to 6 C atoms, for example phenylthio, tolylthio, anisylthio and chlorophenylthio, preferably phenylthio and chlorophenylthio; heteroarylthio radicals which may be mentioned are those with 1 to 5 C atoms, preferably 1 to 4 C atoms, for example pyridylthio, furylthio and imidazolylthio, preferably furylthio; acylthio radicals which may be mentioned are those with 1 to 7 C atoms, preferably 1 to 4 C atoms, for example benzoylthio, acetylthio, formylthio, trichloroacetylthio and trifluoroacetylthio, preferably acetylthio, trichloroacetylthio and trifluoroacetylthio; acyl radicals which may be mentioned are those with 1 to 7 C atoms, preferably 1 to 4 C atoms, for example acetyl, formyl, propionyl, benzoyl, phenylacetyl, chloroacetyl, dichloroacetyl, trichloroacetyl, chlorophenylcarbonyl, trifluoroacetyl and chlorocarbonyl, preferably acetyl, formyl, chloroacetyl, dichloroacetyl, trichloroacetyl, trifluoroacetyl and chlorocarbonyl; thioacyl radicals which may be mentioned are those with 1 to 7 C atoms, preferably 1 to 4 C atoms, for example thioacetyl, thiobenzoyl and trichlorothioacetyl, preferably thioacetyl; acylamino radicals which may be mentioned are those with 1 to 8 C atoms, preferably 1 to 7 C atoms, for example formylamino, acetylamino, trichloroacetylamino, trifluoroacetylamino, benzoylamino, tolylcarbonylamino and chlorophenylcarbonylamino, preferably acetylamino, trifluoroacetylamino and benzoylamino.

Saturated or unsaturated optionally substituted isocyclic or heterocyclic carbon rings (O, S and N hetero atoms) with up to 8 carbon atoms which may be mentioned are: benzo, naphthaleno, thieno, furano, pyrrolo, pyridino, cyclohexano, cyclopentano, oxolano and dioxolano, preferably benzo and cyclohexano.

Halogens which are mentioned are fluorine, chlorine, bromine and iodine, preferably fluorine, chlorine and bromine and particularly preferably chlorine.

Particularly preferred radicals $R^1$ to $R^4$ are hydrogen, methyl, n-propyl, n-tridecyl, benzyl, trifluoromethyl, phenyl, furyl, methoxy, phenoxy, acetyl, methylthio, phenylthio, acetyl, formyl, chlorocarbonyl, nitro and chlorine and the combinations of the radicals amongst themselves in a benzene ring.

Especially preferred radicals $R^1$–$R^4$ are hydrogen, methyl, chlorine and methoxy.

Preferred radicals Y which may be mentioned are: hydrogen, methyl, ethyl, n-propyl, isopropyl, n-butyl, isobutyl, tert.-butyl, benzyl, phenyl, formyl, acetyl, benzoyl, trifluoroacetyl and trichloroacetyl.

Especially preferred radicals Y which may be mentioned are: hydrogen, methyl and acetyl.

Preferred cyclic radicals A which may be mentioned are: cyclohexano and cyclopentano.

Preferred cyclic radicals B which may be mentioned are: benzo and naphthaleno.

Examples of the thiazepines to be used according to the invention which may be mentioned by name are: 2,3-dihydro-5H-benzo[b][1,4]thiazepin-4-one, 2-methyl-2,3-dihydro-5H-benzo[b][1,49 thiazepin-4-one, 2-ethyl-2,3-dihydro-5H-benzo[b][1,4]thiazepin-4-one, 2-propyl-2,3-dihydro-5H-benzo[b][1,4]thiazepin-4-one, 3-methyl-2,3-dihydro-5H-benzo[b][1,4]thiazepin-4-one, 2,3-dimethyl-2,3-dihydro-5H-benzo[b][1,4]thiazepin-4-one, 2,2-dimethyl-2,3-dihydro-5H-benzo[b][1,4]thiazepin-4-one, 2-phenyl-2,3-dihydro-5H-benzo[b][1,4]thiazepin-4-one, 5-methyl-2,3-dihydro-5H-benzo[b][1,4]thiazepin-4-one, 5benzyl-2,3-dihydro-5H-benzo[b][1,4]thiazepin-4-one, 5-acetyl-2,3-dihydro-5-H-benzo[b][1,4]thiazepin-4-one, 5-chlorocarbonyl-2,3-dihydro-5H-benzo[b][1,4]thiazepin-4-one, 2-methyl-5-acetyl-2,3-dihydro-5H-benzo[b][1,4]thiazepin-4-one, 2-chloro-2,3-dihydro-5H-benzo[b][1,4]thiazepin-4-one, 2,3-dichloro-2,3-dihydro-5H-benzo[b][1,4]thiazepin-4-one, 2,2,3-trichloro-2,3-dihydro-5H-benzo[b][1,4]thiazepin-4-one, 2,2,3,3-tetrachloro-2,3-dihydro-5H-benzo[b][1,4]thiazepin-4-one, 5-methyl-2,3-dichloro-2,3-dihydro-5H-benzo[b][1,4]thiazepin-4-one, 3-methoxy-2,3-dihydro-5H-benzo[b][1,4]thiazepin-4-one, 7-chloro-2,3-dihydro-5H-benzo[b][1,4]thiazepin-4-one, 6,8-dichloro-2,3-dihydro-5H-benzo[b][1,4]thiazepin-4-one, 6,8-dichloro-2,3-dimethyl-2,3-dihydro-5H-benzo[b][1,4]thiazepin-4-one, 7-chloro-5-acetyl-2,3-dihydro-5H-benzo[b][1,4]thiazepin-4-one, 7-methyl-2,3-dihydro-5H-benzo[b][1,4]thiazepin-4-one, 7-trifluoromethyl-2,3-dihydro-5H-benzo[b][1,4]thiazepin-4-one, 6,8-dimethyl-2,3-dihydro-5H-benzo[b][1,4]thiazepin-4-one, 2,3-dihydro-5H-[2,3]naphthaleno[b][1,4]thiazepin-4-one, 5H-dibenzo[b,f][1,4]thiazepin-4-one, nucleus-chlorinated 5H-dibenzo[b,f][1,4]thiazepin-4-one, 2,3-tetramethylene-2,3-dihydro-5H-benzo[b][1,4]thiazepin-4-one, 6,8-dimethyl-2,3-tetramethylene-2,3-dihydro-5H-benzo[b][1,4]thiazepin-4-one, 3H-5H-benzo[b][1,4]thiazepine-2,4-dione, 3H-5H-benzo[b][1,4]thiazepin-2-one-4-thione, 3H-5H-benzo[b][1,4]thiazepine-2,4-dithione, 2,3-dihydro-5H-benzo[b][1,4]thiazepine-4-thione, 2-methyl-2,3-dihydro-5H-benzo[b][1,4]thiazepine-4-thione, 6,8-dichloro-2,3-dihydro-5H-benzo[b][1,4]thiazepine-5-thione, 5-acetyl-2,3-dihydro-5H-benzo[b]thiazepine-4-thione, 8-acetyl-2,3-dihydro-5H-benzo[b][1,4]thiazepin-4-one, 1-oxo-2,3-dihydro-5H-1$\lambda^4$-benzo[b][1,4]thiazepin-4-one, 1-oxo-2-methyl-2,3-dihydro-5H-1$\lambda^4$-benzo[b][1,4]thiazepin-4-one, 1-oxo-7-chloro-5-methyl-2,3-dihydro-5H-1$\lambda^4$-benzo[b][1,4]thiazepine-4-thione, 1-oxo-2,3-dimethyl-2,3-dihydro-5H-1$\lambda^4$-benzo[b][1,4]thiazepin-4-one, 5,8-diacetyl-2-methyl-2,3-dihydro-5H-benzo[b][1,4]thiazepin-4-one, 5H-benzo[b][1,4]thiazepin-4-one, 2-chloro-5H-benzo[b][1,4]thiazepin-4-one, 2,3-dichloro-5H-benzo[b][1,4]thiazepin-4-one, 2,3,7-trichloro-5H-benzo[b][1,4]thiazepin-4-one, 2,3,8-trichloro-5H-benzo[b][1,4]thiazepin-4-one, 5-acetyl-5H-benzo[b][1,4]thiazepin-4-one, 2-phenyl-5H-benzo[b][1,4]thiazepin-4-one, 2-methyl-5H-benzo[b][1,4]thiazepin-4-one, 1-oxo-2,3-dihydro-5H-1$\lambda^4$-[2,3]naphthaleno[b][1,4]thiazepin-4-one, 5-acetyl-4,5-dihydro-3H-benzo[b][1,4]thiazepin-2-one, 7-chloro-5-acetyl-4,5-dihydro-3H-benzo[b][1,4]thiazepin-2-one, 3-acetoxy-2,3-dihydro-5H-benzo[b][1,4]thiazepin-4-one, 3-acetoxy-2-phenyl-2,3-dihydro-5H-benzo[b][1,4]thiazepin-4-one, 3-acetoxy-2-(4-methoxyphenyl)-2,3-dihydro-5H-benzo[b][1,4]thiazepin-4-one, 3-acetamino-2,3-dihydro-5H-benzo[b][1,4]thiazepin-4-one, 3-acetamino-2-phenyl-2,3-dihydro-5H-benzo[b][1,4]thiazepin-4-one, 8-chloro-3-acetoxy-2,3-dihydro-5H-benzo[b][1,4]thiazepin-4-one, 8-chloro-3-acetoxy-2-(4-methoxyphenyl)-5H-benzo[b][1,4]thiazepin-4-one, 5[2-(dimethylamino)ethyl]-3-acetoxy-2-(4-methoxyphenyl)-5H-benzo[b][1,4]thiazepin-4-one, 2,3,4,5-tetrahydrobenzo[b][1,4]thiazepine, 5-acetyl-2,3,4,5-tetrahydrobenzo[b][1,4]thiazepine, 2,3-dimethyl-2,3,4,5-tetrahydrobenzo[b][1,4]thiazepine, 5-ethyl-2,3,4,5-tetrahydro-benzo[b][1,4]thiazepine, 2-(2-aminophenylthio)-2,3-dihydro-5H-benzo[b][1,4]thiazepin-4-one, 2-n-tridecyl-2,3-dihydro-5H-benzo[b][1,4]thiazepin-4-one, 5-n-pentyl-2,3-dihydro-5H-benzo[b][1,4]thiazepin-4-one, 2-(2-furyl)-2,3-dihydro-5H-benzo[b][1,4]thiazepin-4-one, 2-[3(4)-imidazolyl]-2,3-dihydro-5H-benzo[b][1,4]thiazepin-4-one, 5-phenyl-2,3-dihydro-5H-benzo[b][1,4]thiazepin-4-one, 8-methoxy-2,3-dihydro-5H-benzo[b][1,4]thiazepin-4-one, 8-ethoxy-2,3-dihydro-5H-benzo[b][1,4]thiazepin-4-one, 8-nitro-2,3-dihydro-5H-benzo[b][1,4]thiazepin-4-one, 7,8,9-trichloro-2,3-dihydro-5H-benzo[b][1,4]thiazepin-4-one, 7-sulphoxyl-2,3-dihydro-5H-benzo[b][1,4]thiazepin-4-one, 8-acetamino-2,3-dihydro-5H-benzo[b][1,4]thiazepin-4-one, 8-methyl-2,3-dihydro-5H-benzo[b][1,4]thiazepin-4-one, 8-chloro-6-methyl-2,3-dihydro-5H-benzo[b][1,4]thiazepin-4-one, 6,7,8,9-tetrachloro-2,3-dihydro-5H-benzo[b][1,4]thiazepin-4-one, 4,5-dihydro-2H-benzo[b][1,4]thiazepin-3-one, 7,9-dimethoxy-2,3-dihydro-5H-benzo[b][1,4]thiazepin-4-one, 7,9-dimethyl-2,3-dihydro-5H-benzo[b][1,4]thiazepin-4-one, 7,8-dimethyl-2,3-dihydro-5H-benzo[b][1,4]thiazepin-4-one, 7-methoxy-2,3-dihydro-5H-benzo[b][1,4]thiazepin-4-one, 7,9-dimethyl-2,3-tetramethylene-2,3-dihydro-5H-benzo[b][1,4]thiazepin-4-one, 5-trifluoroacetyl-2,3,4,5-tetrahydro-benzo[b][1,4]thiazepine, 5-trifluoroacetyl-5H-dibenzo[b,f][1,4]thiazepine, 2,3-dihydro-5H[1,2]naphthaleno[b][1,4]thiazepin-4-one and 2,3,7,9-tetramethyl-2,3-dihydro-5H-benzo[b][1,4]-thiazepin-4-one, preferably: 2,3-dihydro-5H-benzo[b][1,4]thiazepin-4-one, 2-methyl-2,3-dihydro-5H-benzo[b][1,4]thiazepin-4-one, 2-ethyl-2,3-dihydro-5H-benzo[b][1,4]thiazepin-4-one, 2-propyl-2,3-dihydro-5H-benzo[b][1,4]thiazepin-4-one, 3-methyl-2,3-dihydro-5H-benzo[b][1,4]thiazepin-4-one, 2,3-dimethyl-2,3-dihydro-5H-benzo[b][1,4]thiazepin-4-one, 5-methyl-2,3-dihydro-5H-benzo[b][1,4]thiazepin-4-one; 5-benzyl-2,3-dihydro-5H-benzo[b][1,4]thiazepin-4-one, 5-acetyl-2,3-dihydro-5H-benzo[b][1,4]thiazepin-4-one, 5-chlorocarbonyl-2,3-dihydro-5H-benzo[b][1,4]thiazepin-4-one, 2-methyl-5- acetyl-2,3-dihydro-5H-dibenzo[b][1,4]thiazepin-4-one, 7-chloro-2,3-dihydro-5H-benzo[b][1,4]thiazepin-4-one, 6,8-dichloro-2,3-dihydro-5H-benzo[b][1,4]thiazepin-4-one, 6,8-dichloro-2,3-dimethyl-2,3-dihydro-5H-benzo[b][1,4]thiazepin-4-one, 7-methyl-2,3-dihydro-5H-benzo[b][1,4]thiazepin-4-one, 7-trifluoromethyl-2,3-dihydro-5H-benzo[b][1,4]thiazepin-4-one, 6,8-dimethyl-2,3-dimethyl-2,3-dihydro-5H-benzo[b][1,4]thiazepin-4-one, 2,3-dihydro-5H-[2,3]napthaleno[b][1,4]thiazepin-4-one, 5H-dibenzo[b,f][1,4]thiazepin-4-one, nucleus-chlorinated 5H-dibenzo[b,f][1,4]thiazepin-4-one, 2,3-tetramethylene-2,3-dihydro-5H-benzo[b][1,4]thiazepin-4-one, 6,8-dimethyl-2,3-tetramethylene-2,3-dihydro-5H-benzo[b][1,4]thiazepin-4-one, 3H-5H-benzo[b][1,4]thiazepine-2,4-dione, 3H-5H-benzo[b][1,4]thiazepin-2-one-4-thione, 3H-5H-benzo[b][1,4]thiazepine-2,4-dithione, 2,3-dihydro-5H-benzo[b][1,4]thiazepine-4-thione, 2-methyl-2,3-dihydro-5H-benzo[b][1,4]thiazepine-4-thione, 5-acetyl-2,3-dihydro-5H-benzo[b][1,4]thiazepine-4-thione, 1-oxo-2,3-dihydro-5H-1$\lambda^4$-benzo[b][1,4]thiazepin-4-one, 1-oxo-7-chloro-5-methyl-2,3-dihydro-5H$\lambda^4$-benzo[b][1,4]thiazepine-4-thione, 1-oxo-2,3-dimethyl-2,3-dihydro-5H-1$\lambda^4$-benzo[b][1,4]thiazepin-4-one, 3-acetoxy-2,3-dihydro-5H-benzo[b][1,4]thiazepin-4-one, 3-acetamino-2,5-dihydro-5H-benzo[b][1,4]thiazepin-4-one, 2,3,4,5-tetrahydrobenzo[b][1,4]thiazepine, 2,3-dimethyl-2,3,4,5-tetrahydrobenzo[b][1,4]thiazepine, 5-ethyl-2,3,4,5-tetrahydrobenzo[b][1,4]thiazepine, 2-n-tridecyl-2,3-dihydro-5H-benzo[b][1,4]thiazepin-4-one, 5-n-pentyl-2,3-dihydro-5H-benzo[b][1,4]thiazepin-4-one, 8-methoxy-2,3-dihydro-5H-benzo[b][1,4]thiazepin-4-one, 8-ethoxy-2,3-dihydro-5H-benzo[b][1,4]thiazepin-4-one, 8-methyl-2,3-dihydro-5H-benzo[b][1,4]thiazepin-4-one, 8-chloro-6-methyl-2,3-dihydro-5H-benzo[b][1,4]thiazepin-4-one, 7,9-dimethoxy-2,3-dihydro-5H-benzo[b][1,4]thiazepin-4-one, 7,9-dimethyl-2,3-dihydro-5H-benzo[b][1,4]thiazepin-4-one, 7,8-dimethyl-2,3-dihydro-5H-benzo[b][1,4]thiazepin-4-one, 7-methoxy-2,3-dihydro-5H-benzo[b][1,4]thiazepin-4-one, 7,9-dimethyl-2,3-tetramethylene-2,3-dihydro-5H-benzo[b][1,4]thiazepin-4-one, 2,3-dihydro-5H-[1,2]naphthaleno[b]-[1,4]thiazepin-4-one and 2,3,7,9-tetramethyl-2,3-dihydro-5H-benzo[b][1,4]thiazepin-4-one.

The preparation of the co-catalysts according to the invention is generally known from the literature. The co-catalysts can be prepared in a simple manner, for example in one step from optionally substituted o-amino-thiophenol by heating with optionally substituted acrylic acid (J. Chem. Soc. 1927, 2738), or α,β-unsaturated ketones (Chem. Ber. 90, 2683 (1957)). They are furthermore readily obtainable by cyclization of optionally substituted 2-(o-aminophenylmercapto)-propionic acids (Ber. 56, 1415 (1923)).

Aromatic hydrocarbons which can be used according to the invention and are mentioned as preferred are: toluene, ethylbenzene, propylbenzene, cumene, tert.-butylbenzene and phenylcyclohexane. Toluene is preferred.

The process according to the invention is carried out in the liquid phase, it being possible for the aromatic hydrocarbon to be used in liquid form or if appropriate in dilution with an inert solvent. The liquid undilute form is preferred.

Chlorine is preferably used as the chlorinating agent in the process according to the invention. The chlorine is passed in liquid or gaseous form into the reaction mixture. Gaseous chlorine is preferred. However, chlorinating agents other than chlorine can also be used. These are chlorine-containing compounds which release chlorine under the reaction conditions. Sulphuryl chloride may be mentioned as an example.

Reduced, increased or normal pressure is possible as the reaction pressure, and normal pressure is preferred.

The degree of chlorination is preferably not more than 1. Higher degrees of chlorination are possible but usually are not advantageous since they lead to the formation of undesired polychlorinated products.

The reaction can be carried out at temperatures from the solidification point to the boiling point of the reaction mixture. The reaction temperature is usually 0° to 100° C., preferably 20°–80° C. and particularly preferably 40°–60° C.

All the known Friedel-Crafts catalysts can be used according to the invention as Friedel-Crafts catalysts. The following Friedel-Crafts catalysts may be mentioned as examples: antimony chlorides, antimony oxychlorides, aluminum chloride, iron(II) chloride, iron(III) chloride, tellurium chlorides, molybdenum chlorides, tungsten chlorides, titanium chlorides, zinc chloride, tin chlorides, boron chloride and/or boron trifluoride.

The Friedel-Crafts catalysts which can be used according to the invention furthermore also include elements and elemental compounds which form a Lewis acid or have the function of a Lewis acid during the chlorination, for example antimony, iron, lead, tin, zinc, molybdenum, tellurium and aluminium or oxides, sulphides or carbonyls thereof, and boron-containing compounds, such as antimony oxides, iron oxides, iron sulphides, lead sulphides, tin sulphides, zinc sulphides, iron carbonyls, molybdenum carbonyls and/or boron phosphate. Instead of the chlorides mentioned, the bromides and if appropriate also the fluorides or iodides of the elements mentioned can be used according to the invention. Antimony chlorides, aluminium chloride, iron, iron oxides, iron sulphides, iron carbonyls and/or iron(III) chloride are preferred. Iron(III) chloride is particularly preferred.

The amounts in which the Friedel-Crafts catalysts to be used according to the invention are employed can be varied within wide limits. The catalyst action already manifests itself with additions of 0.0005% by weight. 5% by weight of more of Friedel-Crafts catalyst can also be added, but these high amounts in general provide no advantage.

The Friedel-Crafts catalysts are usually added in an amount of about 0.001 to 0.5% by weight, preferably 0.01 to 0.10% by weight, based on the toluene employed.

The co-catalysts which can be used according to the invention furthermore include all the substances which, under the reaction conditions, can form a compound or mixtures of compounds described by the abovementioned formulae given for the co-catalysts according to the invention. These are, in particular, those compounds which are polyunsaturated in the seven-membered ring. They are furthermore open-chain precursors which can be converted into the co-catalysts according to the invention by cyclization.

The co-catalysts which can be used according to the invention furthermore include all the substances which can be formed by reaction of the abovementioned co-catalysts according to the invention with chlorine or hydrogen chloride under the reaction conditions of the chlorination of the aromatic hydrocarbons. This particularly applies to the hydrochlorides of the abovementioned co-catalysts according to the invention.

It is also possible for the co-catalysts to be used in the process according to the invention in combination with other elements or compounds which are not claimed as the co-catalysts. The co-catalysts can be used either individually or as a mixture with one another.

The amounts in which the co-catalysts according to the invention are used can be varied within wide limits. However, amounts of less than 0.0001% by weight are in general not advantageous since the co-catalytic action is then no longer noticeable. 5% by weight or more of co-catalyst can also be added, but these high amounts in general do not provide an advantage. The co-catalysts are usually employed in an amount of about 0.0001 to 0.5% by weight, preferably in an amount of 0.0005 to 0.1% by weight and especially preferably in an amount of 0.001 to 0.01% by weight, based on the aromatic hydrocarbon employed.

The molar ratio of the mixture of at least one Friedel-Crafts catalyst and at least one co-catalyst can be varied within wide limits in the process according to the invention. In general, it is not advantageous to employ the co-catalyst in a large excess in comparison with the Friedel-Crafts catalyst, since otherwise the chlorination reaction is inhibited. It is likewise in general not advantageous to choose too high an excess of Friedel-Crafts catalyst, since otherwise the selectivity-controlling action of the co-catalysts does not appear. The process according to the invention is usually carried out with a molar ratio of Friedel-Crafts catalyst to co-catalyst of about 100:1 to 1:10, the molar ratio of Friedel-Crafts catalyst to co-catalyst is preferably 50:1 to 1:4, and the molar ratio of Friedel-Crafts catalyst to co-catalyst of 20:1 to 1:2 is particularly preferred.

In carrying out the process according to the invention in practice, the addition of the individual components of the catalytic system of Friedel-Crafts catalysts and co-catalysts can be in any desired sequence. The process here can be carried out either continuously or discontinuously. The process according to the invention is carried out, for example, as follows:

The desired aromatic hydrocarbon, for example toluene, is taken and is brought to the desired temperature, for example 50° C. The desired amounts of Friedel-Crafts catalysts and co-catalysts are then added in any desired sequence and gaseous chlorine is passed in with the temperature being kept largely constant, until the desired degree of chlorination is reached. The mixture is then worked up by distillation in the customary manner. The following procedure is also according to the invention: a mixture of alkylbenzene and the desired proportions of catalyst and co-catalyst is prepared and is brought to the desired reaction temperature. A chlorinating agent is then passed in until the desired degree of chlorination is reached. Working up is carried out by distillation in the customary manner. The following procedure is likewise also according to the invention: a solution of the desired Friedel-Crafts catalysts with the co-catalysts in the alkylbenzene is prepared and this is fed to a continuously operating chlorinating apparatus. A chlorinating agent is passed in at a rate such that the desired degree of chlorination is reached. The reaction mixture continuously obtained is worked up by distillation in the customary manner.

In the process according to the invention, it is surprising that the co-catalysts according to the invention, that is to say the compounds of the general formulae given, have such a pronounced co-catalytic action, that is to say that, in combination with the Friedel-Crafts catalysts, they are capable of influencing the o/p ratio of the chlorination of aromatic hydrocarbons such that predominantly the p-compound is formed. Heterocyclic compounds known to date for controlling the o/p selectively always had the form of three linearly fused six-membered rings, that is to say they therefore had a completely different structure. It is furthermore decidedly surprising that the co-catalysts according to the invention give such good yields precisely with the Friedel-Crafts catalyst iron(III) chloride which is exceptionally favourable industrially.

It is likewise surprising that these good results are achieved at industrially very advantageous temperatures of, for example, 40° to 60° C. It is furthermore decidedly surprising that the co-catalysts according to the invention already show their p-selective action at extremely low concentrations, so that the amounts of co-catalysts which need to be used are particularly low. In the especially preferred range of 0.001 to 0.01% by weight, they are powers of ten lower than in the case of the co-catalysts known to date. This fact is exceptionally advantageous both industrially as well as economically and ecologically.

The o/p ratio of 0.64 which can be achieved for toluene by the process according to the invention is the lowest o/p ratio which has been achieved to date with iron(III) chloride catalysis at an average reaction temperature of 40° to 60° C.

It is furthermore exceptionally advantageous industrially that the co-catalysts according to the invention can be prepared in a simple manner by a single reaction step from industrially available starting materials.

The following examples are intended to illustrate the process according to the invention but without limiting it to these examples.

EXAMPLE 1

100 parts by weight of toluene were taken in a reactor, 0.0175 part by weight of FeCl$_3$ and 0.004 part by weight of the co-catalyst of the formula

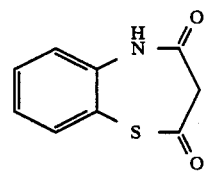

(3H—5H—benzo[b][1,4]-thiazepine-2,4-dione)

were added, with stirring, and the mixture was heated to 55° C. About 94 mol % of gaseous chlorine were uniformly passed in over a period of 5 hours, the temperature being largely kept constant. The residual content of toluene in the reaction mixture was 3.3% by weight and the ratio of ortho-chlorotoluene to para-chlorotoluene (o/p) was 0.75.

EXAMPLE 2

The process of Example 1 was repeated. However, 0.0045 part by weight of the co-catalyst of the formula

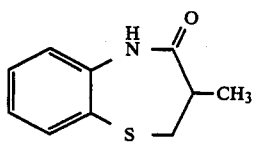

(3-methyl-2,3-dihydro-5H—benzo[b][1,4]thiazepin-4-one)

was added. The toluene content was 3.6% by weight and the o/p ratio was 0.75.

EXAMPLE 3

The process of Example 1 was repeated. However, 0.005 part by weight of the co-catalyst of the formula

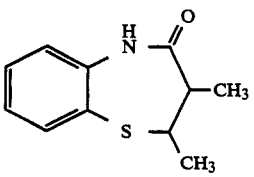

(2,3-dimethyl-2,3-dihydro-5H—benzo[b][1,4]thiazepin-4-one)

was added. The toluene content was 3.0% by weight and the o/p ratio was 0.71.

EXAMPLE 4

The process of Example 1 was repeated. However, 0.009 part by weight of the co-catalyst of the formula

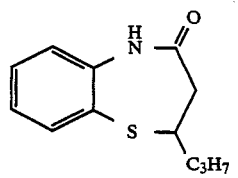

(2-propyl-2,3-dihyro-5H—benzo[b][1,4]thiazepin-4-one)

was added. The toluene content was 4.0% by weight and the o/p ratio was 0.74.

EXAMPLE 5

The process of Example 1 was repeated. However, 0.0025 part by weight of the co-catalyst of the formula

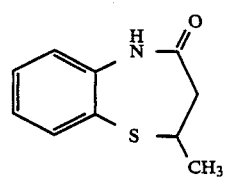

(2-methyl-2,3-dihydro-5H—benzo[b][1,4]thiazepin-4-one)

was added and the mixture was heated to 50° C. The toluene content was 4.1% by weight and the o/p ratio was 0.74.

EXAMPLE 6

The process of Example 1 was repeated. However, 0.004 part by weight of the co-catalyst of the formula

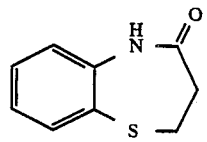

(2,3-dihydro-5H—benzo[b][1,4]thiazepin-4-one was added and the mixture was heated to 40° C. The toluene content was 3.4% by weight and the o/p ratio was 0.74.

EXAMPLE 7

The process of Example 1 was repeated. However, 0.005 part by weight of the co-catalyst of the formula

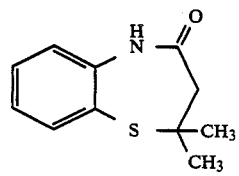

(2,2-dimethyl-2,3-dihydro-5H—benzo[b][1,4]thiazepin-4-one)

was added. The toluene content was 6.9% by weight and the o/p ratio was 1.14.

EXAMPLE 8

The process of Example 1 was repeated. However, 0.005 part by weight of the co-catalyst of the formula

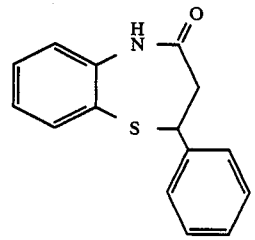

(2-phenyl-2,3-dihydro-5H—benzo[b][1,4]thiazepin-4-one)

was added. The toluene content was 7.2% and the o/p ratio was 1.19.

EXAMPLE 9

The process of Example 1 was repeated. However, 0.005 part by weight of the co-catalyst of the formula

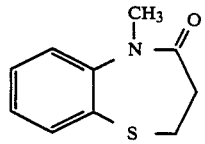

(5-methyl-2,3-dihydro-5H—benzo[b][1,4]thiazepin-4-one)

was added and the mixture was heated to 40° C. The toluene content was 3.4% by weight and the o/p ratio was 0.84.

EXAMPLE 10

The process of Example 1 was repeated. However, 0.005 part by weight of the co-catalyst of the formula

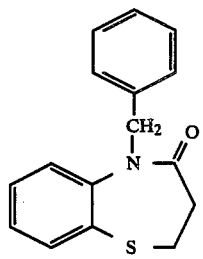

(5-benzyl-2,3-dihydro-5H—benzo[b][1,4]thiazepin-4-one)

was added and the mixture was heated to 50° C. The toluene content was 5.5% by weight and the o/p ratio was 0.92.

EXAMPLE 11

The process of Example 1 was repeated. However, 0.006 part by weight of the co-catalyst of the formula

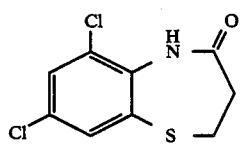

(6,8-dichloro-2,3-dihydro-5H—benzo[b][1,4]thiazepin-4-one)

was added and the mixture was heated to 50° C. The toluene content was 4.4% by weight and the o/p ratio was 0.90.

EXAMPLE 12

The process of Example 1 was repeated. However, 0.005 part by weight of the co-catalyst of the formula

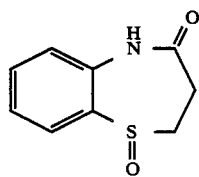

(1-oxo-2,3-dihydro-5H—1$\lambda^4$-benzo[b][1,4]thiazepin-4-one)

was added and the mixture was heated to 50° C. The toluene content was 4.3% by weight and the o/p ratio was 0.76.

EXAMPLE 13

The process of Example 1 was repeated. However, 0.035 part by weight of FeCl$_3$ and 0.06 part by weight of the co-catalyst of the formula

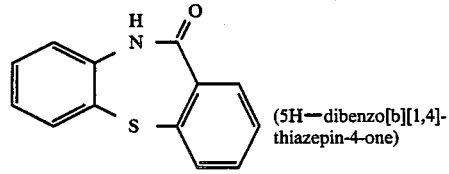

(5H—dibenzo[b][1,4]-thiazepin-4-one)

were added and the mixture was heated to 50° C. The toluene content was 5.0% by weight and the o/p ratio was 0.94.

EXAMPLE 14

The process of Example 1 was repeated, but 0.035 part by weight of FeCl$_3$ and 0.093 part by weight of the co-catalyst of the formula

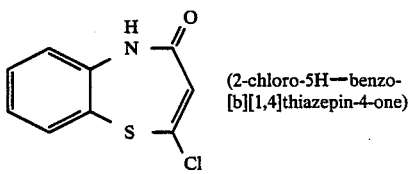

(2-chloro-5H—benzo[b][1,4]thiazepin-4-one)

were added. The toluene content was 8.1% by weight and the o/p ratio was 1.06.

EXAMPLE 15

The process of Example 1 was repeated. However, 0.0046 part by weight of the co-catalyst of the formula

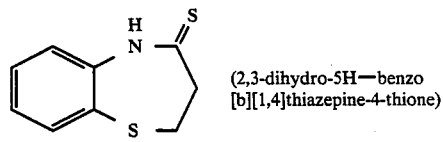

(2,3-dihydro-5H—benzo[b][1,4]thiazepine-4-thione)

was added and the mixture was heated to 50° C. The toluene content was 3.4% by weight and the o/p ratio was 0.76.

EXAMPLE 16 the process of Example 1 was repeated, but 100 parts by weight of cumene were taken, 0.005 part by weight of the co-catalyst of the formula

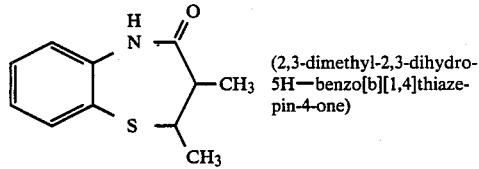

(2,3-dimethyl-2,3-dihydro-5H—benzo[b][1,4]thiazepin-4-one)

was added and the mixture was heated to 50° C. The content of cumene was 3.4% by weight and the ratio of orthochloroisopropylbenzene to para-chloroisopropylbenzene was 0.29.

EXAMPLE 17

The process of Example 1 was repeated. However, 100 parts by weight of ethyl benzene were taken, 0.005 part by weight of the co-catalyst of the formula

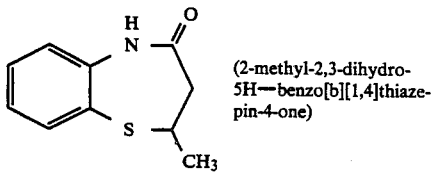

(2-methyl-2,3-dihydro-5H—benzo[b][1,4]thiazepin-4-one)

were added and the mixture was heated to 50° C. The content of ethylbenzene was 4.2% by weight and the ratio of ortho-chloroethylbenzene to para-chloroethylbenzene was 0.54.

EXAMPLE 18

The process of Example 1 was repeated. However, 100 parts by weight of t-butylbenzene were taken, 0.0045 part by weight of the co-catalyst of the formula

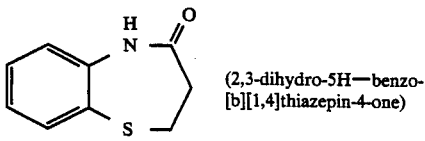

(2,3-dihydro-5H—benzo[b][1,4]thiazepin-4-one)

was added and the mixture was heated to 50° C. The content of t-butylbenzene was 8.9% by weight and the ratio of o-chloro-t-butylbenzene to para-chloro-t-butylbenzene was 0.17.

EXAMPLE 19

The process of Example 1 was repeated. However, 100 parts by weight of cyclohexylbenzene were taken and heated to 50° C. and 0.0045 part by weight of the co-catalyst of the formula

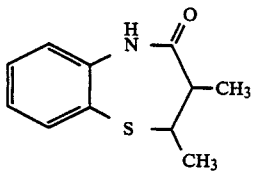

(2,3-dimethyl-2,3-dihydro-5H—benzo[b][1,4]thiazepin-4-one)

was added. The content of cyclohexylbenzene was 2.6% by weight and the ratio of ortho-chlorocyclohexylbenzene to para-chlorocyclohexylbenzene was 0.25.

EXAMPLE 20

A solution of 100 parts by weight of toluene, 0.0175 part by weight of FeCl$_3$ and 0.004 part by weight of the co-catalyst of the formula

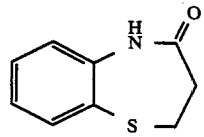

(2,3-dihydro-5H—benzo[b][1,4]thiazepin-4-one)

was prepared at room temperature.

This solution was fed to a continuously operating chlorinating reactor at 40°–43° C., the equivalent amount of chlorination product being removed at the same time. Gaseous chlorine was passed in as the chlorinating agent at a rate such that the conversion was largely constant at 90 mol %. The reaction mixture removed contained 7.1% by weight of toluene and the ratio of ortho-chlorotoluene to para-chlorotoluene was 0.70.

EXAMPLE 21

The process of Example 20 was repeated, but 0.0045 part by weight of the co-catalyst of the formula

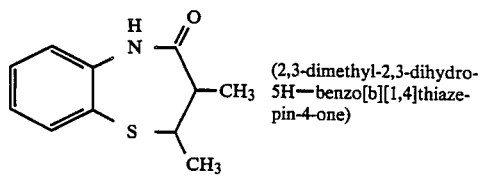

(2,3-dimethyl-2,3-dihydro-5H—benzo[b][1,4]thiazepin-4-one)

was added. The reaction mixture removed contained 7.0% by weight of toluene and the o/p ratio was 0.67.

EXAMPLE 22

The process of Example 20 was repeated, but 0.005 part by weight of the co-catalyst of the formula

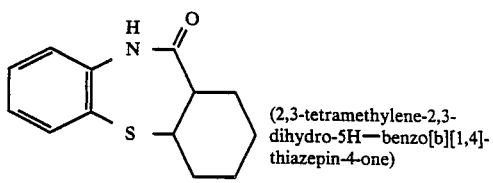

(2,3-tetramethylene-2,3-dihydro-5H—benzo[b][1,4]-thiazepin-4-one)

was added. The reaction mixture removed contained 7.0% by weight of toluene and the o/p ratio was 0.64.

EXAMPLE 23

The process of Example 1 was repeated, but 0.005 part by weight of the co-catalyst of the formula

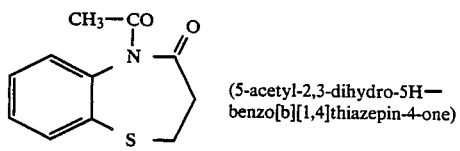

(5-acetyl-2,3-dihydro-5H—benzo[b][1,4]thiazepin-4-one)

was added and the mixture was heated to 50° C. The toluene content was 2.3% by weight and the o/p ratio was 0.77.

EXAMPLE 24

The process of Example 1 was repeated, but 0.004 part by weight of the co-catalyst of the formula

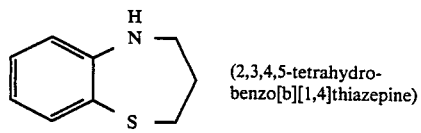

(2,3,4,5-tetrahydro-benzo[b][1,4]thiazepine)

was added and the mixture was heated to 45° C. The residual toluene content was 3.9% by weight and the o/p ratio was 0.91.

EXAMPLE 25

The process of Example 1 was repeated, but 0.0045 part by weight of the co-catalyst of the formula

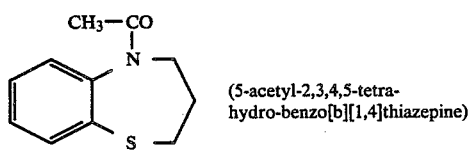

(5-acetyl-2,3,4,5-tetra-hydro-benzo[b][1,4]thiazepine)

was added and the mixture was heated to 50° C. The toluene content was 7.8% by weight and the o/p ratio was 1.35.

EXAMPLE 26

The process of Example 1 was repeated, but 0.008 part by weight of the co-catalyst of the formula

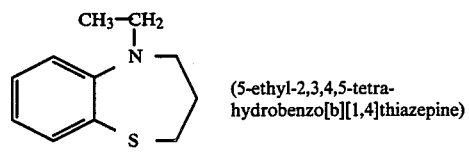

(5-ethyl-2,3,4,5-tetra-hydrobenzo[b][1,4]thiazepine)

was added and the mixture was heated to 50° C. The residual toluene content was 5.7% by weight and the o/p ratio was 0.93.

EXAMPLE 27

The process of Example 1 was repeated, but 0.0045 part by weight of the co-catalyst of the formula

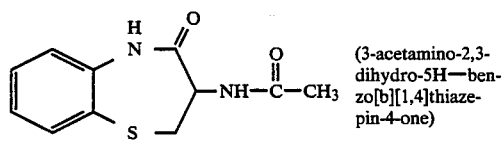

(3-acetamino-2,3-dihydro-5H—benzo[b][1,4]thiazepin-4-one)

was added and the mixture was heated to 50° C. The toluene content was 5.6% by weight and the o/p ratio was 0.99.

EXAMPLE 28

The process of Example 1 was repeated, but 0.008 part by weight of the co-catalyst of the formula

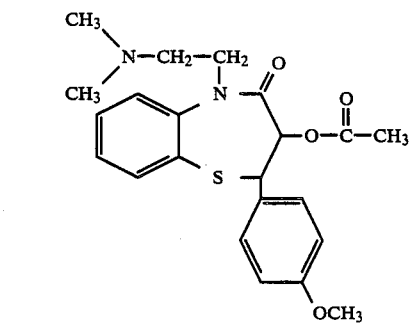

(5[(2-dimethylamino)-ethyl]-3-acetoxy-2-(4-methoxyphenyl)-5H—benzo-[b][1,4]thiazepin-4-one)

was added and the mixture was heated to 50° C. The toluene content was 8.9% by weight and the o/p ratio was 1.34.

EXAMPLE 29

The process of Example 1 was repeated, but 0.005 part by weight of the co-catalyst of the formula

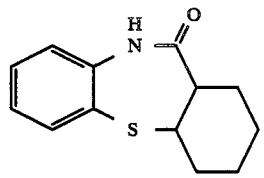

(2,3-tetramethylene-2,3-dihydro-5H—benzo[b][1,4]-thiazepin-4-one)

was added and the mixture was heated to 50° C. The residual toluene content was 4.1% by weight and the o/p ratio was 0.68.

EXAMPLE 30

The process of Example 1 was repeated. However, 0.035 part by weight of $FeCl_3$ and 0.050 part by weight of the co-catalyst of the formula

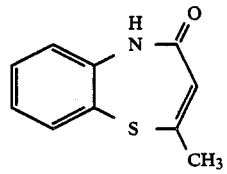

(2-methyl-5H—benzo-[b][1,4]thiazepin-4-one)

were added. The residual toluene was 5.2% by weight and the o/p ratio was 1.44.

EXAMPLE 31

The process of Example 1 was repeated. However, 0.035 part by weight of $FeCl_3$ and 0.013 part by weight of the co-catalyst from Example 6 were added and the mixture was heated to 50° C. The toluene content was 3.5% by weight and the o/p ratio was 0.77.

EXAMPLE 32

The process of Example 1 was repeated. However, 0.001 part by weight of the co-catalyst of Example 6 were added and the mixture was heated to 50° C. The toluene content was 5.3% by weight and the o/p ratio was 0.77.

EXAMPLE 33

The process of Example 1 was repeated. However, 0.0055 part by weight of a mixture of about 95% of the co-catalyst of the formula

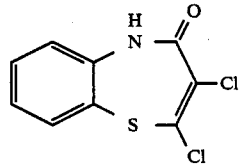

-continued
(2,3-dichloro-5H—benzo-[b][1,4]thiazepin-4-one)

and about 5% of the co-catalyst of the formula

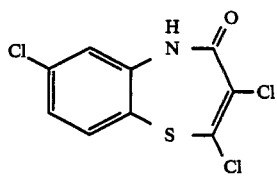

(2,3,7-trichloro-5H—benzo-[b][1,4]thiazepin-4-one)

was added and the mixture was heated to 50° C. The toluene content was 4.6% and the o/p ratio was 1.19.

EXAMPLE 34

The process of Example 1 was repeated, but 0.006 part by weight of the co-catalyst of the formula

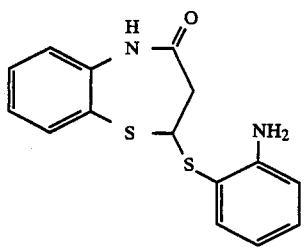

(2-(2-aminophenylthio)-2,3-dihydro-5H—benzo[b][1,4]-thiazepin-4-one)

was added and the mixture was heated to 50° C. The residual toluene content was 3.6% by weight and the o/p ratio was 1.08.

EXAMPLE 35

The process of Example 1 was repeated, but 0.008 part by weight of the co-catalyst of the formula

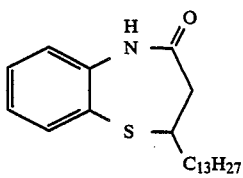

(2-n-tridecyl-2,3-dihydro-5H—benzo[b][1,4]thiazepin-4-one)

was added. The toluene content was 3.5% by weight and the o/p ratio was 0.71.

EXAMPLE 36

The process of Example 1 was repeated. However, 0.0055 part by weight of the co-catalyst of the formula

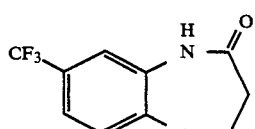

(7-trifluoromethyl-2,3-dihydro-5H—benzo[b][1,4]-thiazepin-4-one)

was added. The toluene content was 4.4% by weight and the o/p ratio was 0.89.

EXAMPLE 37

The process of Example 1 was repeated. However, 0.0045 part by weight of the co-catalyst of the formula

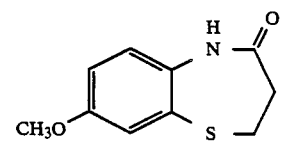

(8-methoxy-2,3-dihydro-5H—benzo[b][1,4]thiazepin-4-one)

was added and the mixture was heated to 45° C. The residual toluene content was 4.0% by weight and the o/p ratio was 0.76.

EXAMPLE 38

The process of Example 1 was repeated. However, 0.0055 part by weight of the co-catalyst of the formula

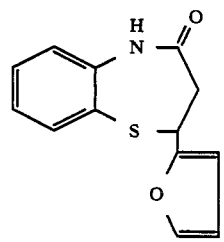

(2-(2-furyl)-2,3-dihydro-5H—benzo[b][1,4]thiazepin-4-one)

was added and the mixture was heated to 50° C. The residual toluene content was 4.4% by weight and the o/p ratio was 1.10.

EXAMPLE 39

The process of Example 1 was repeated. However, 0.0055 part by weight of the co-catalyst of the formula

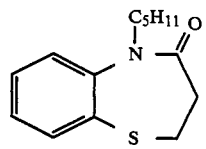

(5-n-pentyl-2,3-dihydro-5H—benzo[b][1,4]thiazepin-4-one)

was added. The residual toluene content was 3.4% by weight and the o/p ratio was 0.99.

EXAMPLE 40

The process of Example 1 was repeated, but 0.0047 part by weight of the co-catalyst of the formula

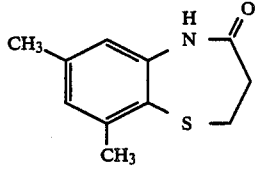

(7,9-dimethyl-2,3-dihydro-5H—benzo[b][1,4]-thiazepin-4-one)

was added and the mixture was heated to 50° C. The residual toluene content was 2.8% by weight and the o/p ratio was 0.71.

EXAMPLE 41

The process of Example 1 was repeated. However, 0.0059 part by weight of the co-catalyst of the formula

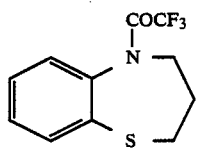

(5-trifluoroacetyl-2,3,4,5-tetrahydro-benzo-[b][1,4]thiazepine)

was added and the mixture was heated to 50° C. The residual toluene content was 3.8% by weight and the o/p ratio was 1.12.

EXAMPLE 42

The process of Example 1 was repeated. However, 0.0069 part by weight of the co-catalyst of the formula

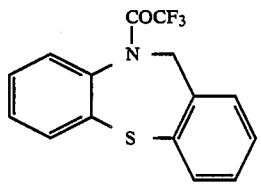

(5-trifluoroacetyl-5H—dibenzo-[b][1,4]thiazepine)

was added and the mixture was heated to 50° C. The residual toluene content was 2.8% by weight and the o/p ratio was 0.97.

EXAMPLE 43

The process of Example 1 was repeated. However, 0.0051 part by weight of the co-catalyst of the formula

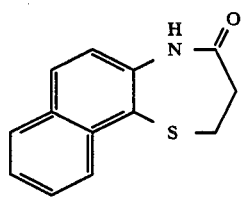

(2,3-dihydro-5H[1,2]-naphthaleno[b][1,4]-thiazepin-4-one)

was added. The residual toluene content was 3.2% by weight and the o/p ratio was 0.76.

EXAMPLE 44

The process of example 20 was repeated. However, 0.0046 part by weight of the co-catalyst of the formula

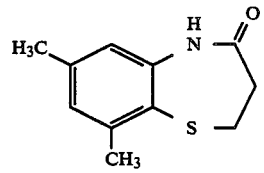

(7,9-dimethyl-2,3-dihydro-5H—benzo[b][1,4]thiazepin-4-one)

was added. The reaction mixture removed contained 7,5% by weight of toluene and the o/p ratio was 0,68.

EXAMPLE 45

The process of example 20 was repeated. However, 0.0053 part by weight of the co-catalyst of the formula

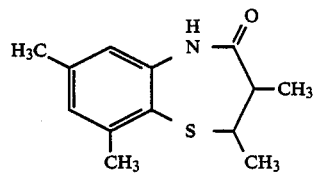

(2,3,7,9-tetramethyl-2,3-dihydro-5H—benzo[b][1,4]thiazepin-4-one)

was added. The reaction mixture removed contained 7,5% by weight of toluene and the o/p ratio was 0,65.

EXAMPLE 46

The process of example 20 was repeated. However, 0.0057 part by weight of the co-catalyst of the formula

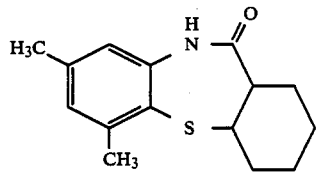

(7,9-dimethyl-2,3-tetramethylene-2,3-dehydro-5-H benzo[b][1,4]thiazepin-4-one)

was added. The reaction mixture removed contained 7.0% by weight of toluene and the o/p ratio was 0.64.

EXAMPLE 47

The process of example 1 was repeated. However, 0.0047 part by weight of the co-catalyst of the formula

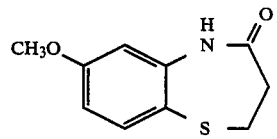

-continued (7-methoxy-2,3-dihydro-5H—benzo[b][1,4]thiazepin-4-one]

was added. The residual toluene content was 3,6% by weight and the o/p ratio was 0,70.

EXAMPLE 48

The process of example 1 was repeated. However, 0.0053 part by weight of the co-catalyst of the formula

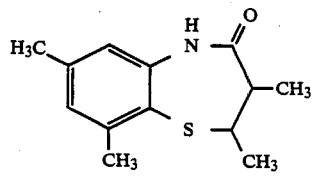

[2,3,7,9-tetramethyl,2,3-dihydro-5H—benzo[b][1,4] thiazepin-4-one)

was added. The residual toluene content was 3,1% by weight and the o/p ratio was 0,67.

EXAMPLE 49

The process of example 1 was repeated. However, 0.0057 part by weight of the co-catalyst of the formula

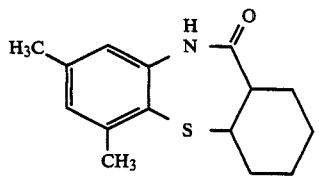

(7,9-dimethyl-2,3-tetramethylene-2,3-dihyro-5H— benzo[b][1,4]-thiazepin-4-one)

was added. The residual toluene content was 3.4% by weight and the o/p ratio was 0.64.

EXAMPLE 50

(Comparison Example)

0.07 part by weight of FeCl₃ and 0.29 part by weight of the phenoxathiine derivative prepared in accordance with the instructions of European Pat. No. 0,173,222 were dissolved in 100 parts by weight of toluene. About 94 mol % of gaseous chlorine were passed in at 50° C., with stirring. The residual content of toluene was 7.9% and the o/p ratio was 0.88.

EXAMPLE 51

(Comparison Example)

The process of Example 50 was repeated. 0.0175 part by weight of FeCl₃ and 0.008 part by weight of the phenoxathiine derivative prepared in accordance with the instructions of European Pat. No. 0,173,222 were dissolved in 100 parts by weight of toluene. About 94 mol % of gaseous Cl₂ was passed in at 50° C., with stirring. The residual content of toluene was 6.4% by weight and the o/p ratio was 1.26.

EXAMPLE 52

(Comparison Example)

The process of Example 50 was repeated. 0.0175 part by weight of FeCl₃ and 0.0065 part by weight of the co-catalyst of the formula

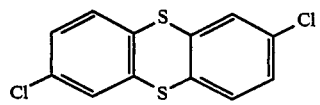

(2,7-dichlorothianthrene)

mentioned in Example 4 of U.S. Pat. No. 4,031,147 were dissolved in 100 parts by weight of toluene. The solution was heated to 50° C. and about 94 mol % of gaseous Cl₂ was passed in, with stirring. The residual toluene content was 6.7% by weight and the o/p ratio was 1.55.

EXAMPLE 53

(Comparison Example)

The process of Example 50 was repeated. 0.0175 part by weight of FeCl₃ and 0.006 part by weight of the co-catalyst of the formula

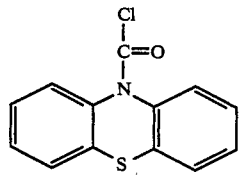

(N—chlorocarbonylphenothiazine)

mentioned in Example 1 of European Pat. No. 0,126,669 were dissolved in 100 parts by weight of toluene. The solution was heated to 50° C. and about 94 mol % of gaseous chlorine were passed in, with stirring. The residual toluene content was 5.6% by weight and the o/p ratio was 1.04.

What is claimed is:

1. A process for nucleus-chlorination of an aromatic hydrocarbon compound of the formula

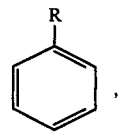

wherein

R denotes an alkyl or cycloalkyl radical with up to 12 C atoms, comprising reacting said aromatic hydrocarbon with a chlorinating agent selected from the group consisting of a liquid chlorine, gaseous chlorine and sulphuryl chloride at a temperature of 0° to 100° C. in the presence of Friedel-Crafts catalysts and in the presence of co-catalysts in the liquid phase, wherein thiazepines are used a co-catalysts and wherein the degree of chlorination is not more than 1.

2. A process according to claim 1, characterized in that thiazepines of the formulae

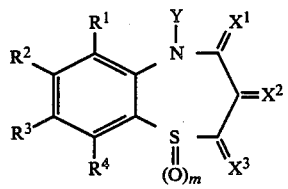

or

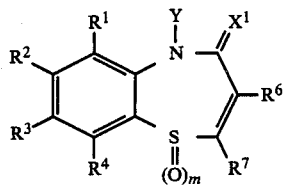

or

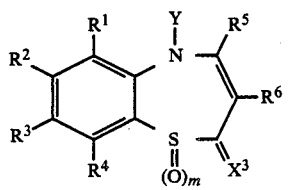

or

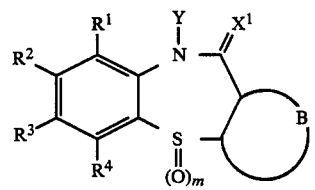

or

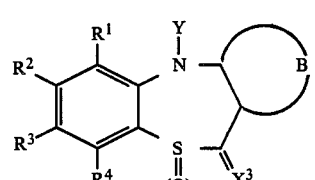

or

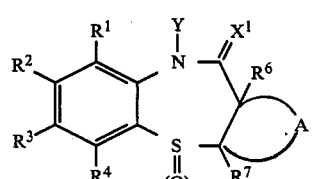

or

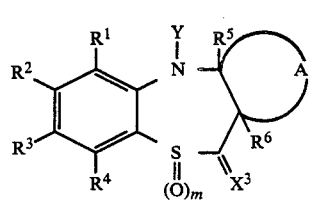

wherein $R^1$, $R^2$, $R^3$ and $R^4$ are identical or different and represent hydrogen, hydroxyl, amino, cyano, halogen, nitro, nitroso, sulphonyl, sulphoxyl, tosyl, mercapto, carboxyl, carboxyamide, carbalkoxy, dithiocarboxyl, thiocarboxyamide, dithiocarbalkoxy or optionally substituted alkyl, aryl, heteroaryl, alkoxy, aryloxy, heteroaryloxy, acyloxy, alkylthio, arylthio, heteroarylthio, acylthio, acyl, thioacyl or acylamino, or amongst themselves form one or more saturated or unsaturated optionally substituted isocyclic or heterocyclic carbon rings with up to 8 C atoms, Y denotes hydrogen or optionally substituted alkyl, aryl, heteroaryl, acyl, thioacyl, acyloxy, arylamino or acylamino, $X^1$, $X^2$ or $X^3$ denote the following groupings:

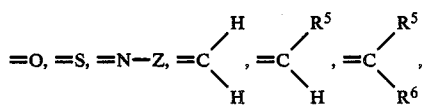

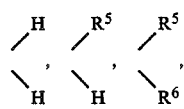

wherein $R^5$, $R^6$ and $R^7$ are identical or different and have the meaning of $R^1$ to $R^4$, with the exception that they do not form a cyclic ring amongst themselves and Z has the meaning of Y, with the exception that Z is not H, A denotes the fusing-on of an optionally substituted saturated isocyclic or heterocyclic ring with up to 8 C atoms, B denotes the fusing-on of an optionally substituted unsaturated isocyclic or heterocyclic ring with up to 8 C atoms and m denotes 0 or 1.

3. A process according to claim 2, characterized in that thiazepines of the formulae

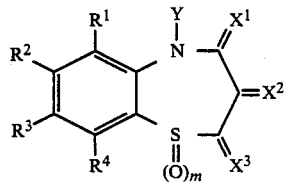

or

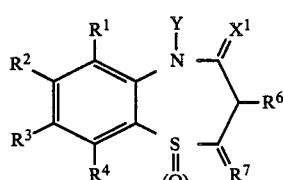

or

-continued

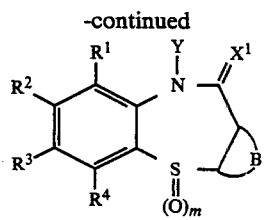

or

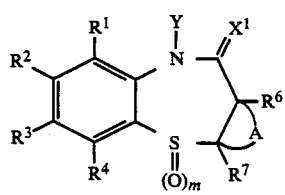

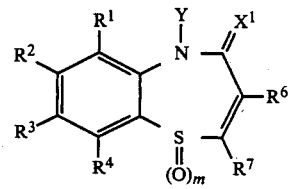

or

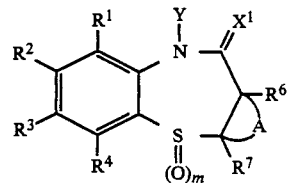

wherein
R¹, R², R³ and R⁴ are identical or different and represent hydrogen, hydroxyl, amino, cyano, halogen, nitro, nitroso, sulphonyl, sulphoxyl, tosyl, mercapto, carboxyl, carboxyamide, carbalkoxy, dithiocarboxyl, thiocarboxylamide, dithiocarbalkoxy or optionally substituted alkyl, aryl, heteroaryl, alkoxy, aryloxy, heteroaryloxy, acyloxy, alkylthio, arylthio, heteroarylthio, acylthio, acyl, thioacyl or acylamino, or amongst themselves form one or more saturated or unsaturated optionally substituted isocyclic or heterocyclic carbon rings with up to 8 C atoms, Y denotes hydrogen, or optionally substituted alkyl, aryl, heteroaryl, acyl, thioacyl, acyloxy, arylamino or acylamino, X¹, X² or X³ denote the following groupings:

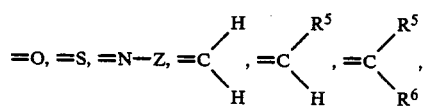

and wherein
R⁵, R⁶ and R⁷ are identical or different and have the meaning of R¹ to R⁴, with the exception that they do not form a cyclic ring amongst themselves, Z has the meaning of Y, with the exception that Z is not H, A denotes the fusing-on of an optionally substituted saturated isocyclic or heterocyclic ring with up to 8 C atoms, B denotes the fusing-on of an optionally substituted unsaturated isocyclic or heterocyclic ring with up to 8 C atoms and m denotes 0 or 1,
are used.

4. A process according to the claim 3, characterized in that thiazepines of the formulae wherein
R¹, R², R³ and R⁴ are identical or different and represent hydrogen, hydroxyl, amino, cyano, halogen, nitro, nitroso, sulphonyl, sulphoxyl, tosyl, mercapto, carboxyl, carboxyamide, carbalkoxy, dithiocarboxyl, thiocarboxylamide, dithiocarbalkoxy or optionally substituted alkyl, aryl, heteroaryl, alkoxy, aryloxy, heteroaryloxy, acyloxy, alkylthio, arylthio, heteroarylthio, acylthio, acyl, thioacyl or acylamino, or amongst themselves form one or more saturated or unsaturated optionally substituted isocyclic or heterocyclic carbon rings with up to 8 C atoms, Y denotes hydrogen or optionally substituted alkyl, aryl, heteroaryl, acyl, thioacyl, acyloxy, arylamino or acylamino, X¹ denotes the following groupings:

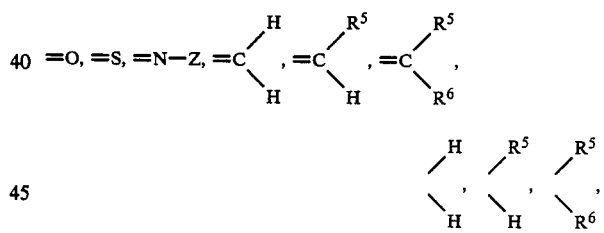

wherein
R⁵, R⁶ and R⁷ are identical or different and have the meaning of R¹ to R⁴, with the exception that they do not form a cyclic ring amongst themselves, Z has the meaning of Y, with the exception that Z is not H, A denotes the fusing-on of an optionally substituted saturaed isocyclic or heterocyclic ring with up to 8 C atoms and m denotes 0 or 1,
are used.

5. A process according to claim 1, characterized in that the amount of co-catalyst used is 0.0001 to 0.5% by weight, based on the aromatic hydrocarbon employed.

6. A process according to claim 5, characterized in that the amount of co-catalyst used in 0.001 to 0.1% by weight, based on the aromatic hydrocarbon employed.

7. A process according to claim 1, characterized in that hydrocarbons for nucleus-chlorination are toluene, ethylbenzene, propylbenzene, cumene, tert.-butylbenzene or phenylcyclohexane.

8. A process according to claim 7, characterized in that the hydrocarbon for nucleus-chlorination is toluene.

9. A process according to claim 1, characterized in that gaseous chlorine is used as chlorinating agent.

10. A process according to claim 1, characterized in that the reaction is carried out at a temperature from the soldification point to the boiling point of the reaction mixture.

11. A process according to claim 1, characterized in that the reaction is carried out at a temperature of 20°-80° C.

12. A process according to claim 11, characterized in that the reaction is carried out at a temperature of 40°-60° C.

13. A process according to claim 1, characterized in that an antimony chloride or oxychloride, aluminum chloride, iron(II) or iron(III)chloride, a tellurium chloride, a molybdenum chloride, a tungsten chloride, a titanium chloride, zinc chloride, a tin chloride or boron chloride or tifluoride is used as Friedel-Crafts catalyst.

14. A process according to claim 1, characterized in that a substance which, under the reaction conditions, can form a thiazepin is used a co-catalyst.

15. A process according to claim 14, characterized in that a compound which is polyunsaturated in the seven-membered ring is used as a substance which, under the reaction conditions, forms a thiazepin.

16. A process according to claim 14, characterized in that an open-chain precursor is used which, under the reaction conditions, forms a thiazepin.

17. A process according to claim 1, characterized in that a mixture of thiazepines is used as co-catalyst.

18. A process according to claim 1, wherein predominately a p-compound is formed.

* * * * *